US008097605B2

(12) United States Patent
Maus et al.

(10) Patent No.: US 8,097,605 B2
(45) Date of Patent: *Jan. 17, 2012

(54) COMBINATION OF ANTICHOLINERGICS AND INHIBITORS OF PHOSPHODIESTERASE TYPE 4 FOR THE TREATMENT OF RESPIRATORY DISEASE

(75) Inventors: Joachim Maus, Muehlheim (DE); Peter Juergen Cnota, Bad Homburg (DE); Istvan Szelenyi, Schwaig (DE); Beatrix Fyrnys, Muehlheim (DE)

(73) Assignee: Meda Pharma GmbH & Co. KG, Bad Homburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/365,003

(22) Filed: Feb. 3, 2009

(65) Prior Publication Data

US 2009/0136429 A1    May 28, 2009

Related U.S. Application Data

(63) Continuation of application No. 11/485,486, filed on Jul. 13, 2006, now abandoned, which is a continuation of application No. 11/051,463, filed on Feb. 7, 2005, now abandoned.

(60) Provisional application No. 60/541,955, filed on Feb. 6, 2004.

(51) Int. Cl.
*A61K 31/56* (2006.01)
*A61K 31/44* (2006.01)

(52) U.S. Cl. .................. 514/171; 514/352; 514/826

(58) Field of Classification Search .................. 514/171, 514/352, 826
See application file for complete search history.

(56) References Cited

U.S. PATENT DOCUMENTS

| 5,712,298 | A  | 1/1998  | Amschler et al. |
| 6,086,914 | A  | 7/2000  | Weinstein et al. |
| 6,204,285 | B1 | 3/2001  | Fabiano et al. |
| 6,384,038 | B1 | 5/2002  | Rubin |
| 6,475,467 | B1 | 11/2002 | Keller et al. |
| 6,645,466 | B1 | 11/2003 | Keller et al. |
| 7,258,118 | B2 | 8/2007  | Goede et al. |
| 2001/0025040 | A1 | 9/2001 | Poppe et al. |
| 2001/0027789 | A1 | 10/2001 | Goede et al. |
| 2002/0115681 | A1 | 8/2002 | Bozung et al. |
| 2002/0151597 | A1 | 10/2002 | Banerjee et al. |
| 2003/0068280 | A1 | 4/2003 | Bannister et al. |
| 2003/0119802 | A1 | 6/2003 | Gavin |
| 2004/0002548 | A1 | 1/2004 | Bozung et al. |
| 2004/0028734 | A1 | 2/2004 | Bannister et al. |
| 2004/0028958 | A1 | 2/2004 | Assink et al. |
| 2004/0038958 | A1 | 2/2004 | Rundfeldt et al. |
| 2004/0053902 | A1 | 3/2004 | Smith |
| 2005/0288265 | A1 | 12/2005 | Locher et al. |
| 2006/0081246 | A1 | 4/2006 | Goede et al. |
| 2006/0147382 | A1 | 7/2006 | Bundschuh et al. |

FOREIGN PATENT DOCUMENTS

| EP | 1449528 | 8/2004 |
| WO | WO-01/76575 A | 10/2001 |
| WO | WO-02/069945 A | 9/2002 |
| WO | WO-02/078671 | 10/2002 |
| WO | WO-02/096423 A | 12/2002 |
| WO | WO-02/096463 A | 12/2002 |
| WO | WO-03/011274 A | 2/2003 |
| WO | WO-2004019984 | 3/2004 |
| WO | WO-2004/084897 | 10/2004 |
| WO | WO-200505999 | 6/2005 |

OTHER PUBLICATIONS

Mueller et al. ("Development of powder for inhalation with R,R-glycopyrrolate as active ingredient for the delivery from novel multidose dry powder inhaler", European Respiratory Society Annual Congress 2003, Sep. 2003, abstract 2977).*

Santing et al., "Phosphodiesterase inhibitors reduce bronchial hyper-reactivity and airway inflammation in unrestrained guinea pigs", European Journal of Pharmacology, vol. 275, No. 1, pp. 75-82 (Feb. 4, 1992).*

Reid, P., "Roflumilast", Current Opinion in Investigational Drugs, Current Drugs, London, GB, vol. 3, No. 8, Aug. 2002, pp. 1165-1170, XP001119630, ISSN: 0967-8298 Abstract.

Reid, P., "Roflumilast", Current Opinion in Investigational Drugs, Current Drugs, London, GB, vol. 3, No. 8, Aug. 2002, pp. 1165-1170.

Pahl, Andreas, Possible Synergistic Effects f R, S/S,R-glycopyrolate and Tiotropium with the Glucocorticoid Budesonide, Viatris; No. 2006-03, Jul. 19, 2006.

Austen et al., at p. 856 (Austen et al., Samter's Immunologic Diseases. Philadelphia: Lippincott Williams & Wilkins, 2001, pp. 855-56.

Brostroff et al., Clinical Immunology. London: Gower Medical Publishing, 1991, p. 17.1.

Gennaro, Alfonso. Remington's: Pharmaceutical Sciences. Easton, PA:Mack Publishing Co., 1985, p. 728.

Roitt et al. Immunology. 3rd Ed. St. Louis: Mosby, 193, p. 19.13.

(Continued)

*Primary Examiner* — Kevin E Weddington
(74) *Attorney, Agent, or Firm* — Venable LLP; Keith G. Haddaway

(57) ABSTRACT

The present invention relates to a combination of an inhaled/oral PDE 4 inhibitor in combination with inhaled anticholinergic bronchodilators (muscarinic receptor antagonists), preferentially Roflumilast or AWD-12-281 and R,R-glycopyrrolate, for symptomatic or prophylactic treatment of respiratory diseases, especially those accompanied by obstruction or inflammation such as chronic obstructive pulmonary disease (COPD) or asthma. It further comprises the presentation of this combination in a locally applied (inhaled) formulation and application in an inhalation device for instance in the Novolizer®.

16 Claims, No Drawings

OTHER PUBLICATIONS

Herbst et al. "Selective oral epidermal growth factor receptor tyrosine kinase inhibitor ZD1839 is generally well-tolerated and has activity in non-small cell lung cancer and other solid tumors: results of a Phase I trial" Journal of Clinical Oncology, Sep. 15, 2002, vol. 20, No. 18, pp. 3815-3825.

Finsnes et al., "Leukotriene antagonism reduces the generation of endothelin-I and interferon-gamma and inhibits eosinophilic airway inflammation" Respiratory Medicine, 2002, vol. 96, pp. 901-906.
International Search Report dated Nov. 23, 2005, issued in PCT/EP2005/000649.

* cited by examiner

COMBINATION OF ANTICHOLINERGICS AND INHIBITORS OF PHOSPHODIESTERASE TYPE 4 FOR THE TREATMENT OF RESPIRATORY DISEASE

CROSS REFERENCE TO RELATED APPLICATIONS

This application is a Continuation of U.S. patent application Ser. No. 11/485,486, filed Jul. 13, 2006, which is a Continuation of Ser. No. 11/051,463, filed Feb. 7, 2005, which claims benefit of U.S. Provisional Patent Application No. 60/541,955, filed Feb. 6, 2004, the contents of each of which are incorporated by reference in their entirety.

The present invention relates to a combination of an inhaled/oral PDE 4 inhibitor in combination with inhaled anticholinergic bronchodilators (muscarinic receptor antagonists), preferentially Roflumilast or AWD-12-281 and R,R-glycopyrrolate, for symptomatic or prophylactic treatment of respiratory diseases, especially those accompanied by obstruction or inflammation such as chronic obstructive pulmonary disease (COPD) or asthma. It further comprises the presentation of this combination in a locally applied (inhaled) formulation and application in an inhalation device for instance in the Novolizer®.

Asthma bronchiale, affecting as many as 10% of individuals in industrialized nations, is characterized by bronchoconstriction, chronic airway inflammation, airway hyperreactivity, and mucosal edema. Airway remodeling and altered noncholinergic, nonadrenergic neurotransmission may contribute to irreversible airway obstruction and reduction of pulmonary function. Asthma bronchiale has emerged as a major public health problem worldwide over the past 20 years. Although data indicate that current asthma therapies led to limited decreases in death rates, it continues to be a significant health care problem (Mannino et at., Surveill Summ 2002; 51:1-13). It still is one of the leading causes of preventable hospitalization worldwide and accounts for several million lost workdays. Along with the increase in asthma prevalence, the costs associated with this disease have also risen dramatically.

Chronic obstructive pulmonary disease (COPD) is also very common. This disease is characterized by progressive airflow limitations accompanied by inflammatory reactions. From a review of data from all over the world, it is clear that tobacco is not the only cause of COPD. The worldwide increasing age is also a certain risk factor. The prevalence of COPD varies, it may be between 3% and 10% with a steadily increasing trend. Although COPD is a leading cause of illness and death, its recognition as a public health problem has been slow to evolve despite the rising mortality rate for COPD and the decline in death rates for most of the cardiovascular diseases (Hurd, Chest 2000; 117(2 Suppl):1S-4S). Additionally, COPD imparts substantial economic burden on individuals and society.

There is now strong evidence that airway inflammation is a predominant underlying problem in patients with asthma. The pathophysiology of asthma involves an intricate network of molecular and cellular interactions, although the contribution of each individual factor is probably different from patient to patient depending on the setting and stimulus. Major participants in the development of an asthma phenotype include the triggering stimuli such as the allergens themselves, cells such as T cells, epithelial cells and mast cells that produce a variety of cytokines including IL-5, GM-CSF, IL-3, IL-4 and IL-13 and chemokines such as eotaxin, adhesion molecules, etc. Recent advances in understanding the inflammatory and immunological mechanisms of asthma have indicated many potential therapeutic avenues that may prevent or reverse abnormalities that underlie asthma.

At present, pharmacotherapy is the mainstay of treatment of asthma. Short- and long-acting inhaled β2-adrenoceptor agonists are available. The short-acting β2-adrenoceptor agonists are now used on an on-demand-basis for rapid relief of symptoms. In recent years, long-acting inhaled β2-adrenoceptor agonists have had an increasing role in the management of asthma, particularly in patients with moderate to severe asthma. Antimuscarinic drugs are rather less efficacious in the relief of an asthma attack than the β2-adrenoceptor agonists (Rodrigo and Rodrigo, Chest 2002; 121:1977-87). However, with the introduction of the new anticholinergic tiotropium, the use of anticholinergics in respiratory diseases will enormously increase. Inhaled glucocorticoids have become the mainstay of therapy in chronic asthma. They are the most clinically effective treatment available but can produce serious secondary effects and, moreover, be inefficient in corticosteroid-resistant asthmatics.

In general, much less is known about the pathogenesis of COPD than that of asthma. Recent studies have greatly expanded the understanding of pathogenetic mechanisms underlying COPD. Thus, there is consent that COPD is also an inflammatory disease. From the present pathogenetical point of view, neutrophil granulocytes, CD8+ lymphocytes and macrophages with their mediators play probably crucial roles in the pathogenesis of COPD.

The current management is focused on the improvement of the lung function of patients suffering from COPD. The first step is in this process smoking cessation. There is evidence that smoking reduction or cessation may result in improvement of some respiratory parameters. Bronchodilators (β2-adrenoceptor agonists and anticholinergics) are now the mainstay of symptomatic therapy. Short- and long-acting β2-adrenoceptor agonists such as salbutamol, fenoterol, salmeterol, formoterol are established therapeutics in the symptomatic COPD management. Of the short-acting antimuscarinic drugs, ipratropium is widely used. Recently, tiotropium, a long-acting anticholinergic with a certain preference to $M_3$-muscarinic receptors has now been introduced world-wide (Hansel and Barnes, Drugs Today (Barc) 2002; 38:585-600). Anticholinergic agents can effectively be used in the treatment of COPD in horses, as well. Ipratropium at a dose of 2400 µg/horse is an effective bronchodilator in horses with COPD (Duvivier et al., Equine Vet J 1999; 31:20-4, Bayly et al., Equine Vet J. 2002 January; 34(1):36-43). At present, the anti-inflammatory therapy of COPD is unsolved. The use of systemic and inhaled glucocorticoids for COPD has increased appreciably over the past 20 years. They have been tested on the premise that interference with inflammation in COPD should alter the course of the disease. Although inhaled corticosteroids have a proven benefit in the management of asthma, but until recently, their efficacy in non-asthmatic, smoking-related COPD was not evidence-based (Bonay et al., Drug Saf 2002; 25:57-71). Inhaled glucocorticoids have relatively little impact on the inflammatory processes that characterize COPD (Adcock and Chung, Curr Opin Investig Drugs 2002; 3:58-60). Therefore, they are indicated if there is a significant bronchodilator response or the patient has a more severe disease with frequent exacerbations (Alsaeedi et al., Am J Med 2002; 113:59-65).

Airflow obstruction and airway inflammation are features of asthma as well as COPD. Although the airway inflammation in asthma and COPD, respectively, involve different cell types, both diseases are of chronic inflammatory nature associated with cellular infiltration and activation. While bronchial asthma is predominantly characterized by eosinophils and CD4 lymphocytes, neutrophil granulocytes, CD8 lymphocytes and macrophages appear to play a major role in the pathogenesis of COPD. Thus, PDEs that are involved in smooth muscle relaxation and are also found in eosinophils as well as neutrophils and other inflammatory and immunocompetent cells probably constitute an essential element of the progress of both diseases. Many of the events and mechanisms involved in the pathogenesis of these diseases are inhibited by the activation of the cyclic nucleotide-signaling pathway. Thus, an increase in intracellular CAMP interferes with lymphocyte, eosinophil, neutrophil, and mast cell activation, and blocks cytokine production, cell replication, and cell chemotaxis to sites of inflammation. In addition, activation of the cAMP signaling pathway in airway smooth muscle cells promotes relaxation and blocks smooth muscle cell replication (Tomlinson et al., Biochem Pharmacol 1995; 49: 1809-19), thus preventing the airway remodeling observed in the chronic stage of the diseases.

PDE4 belongs to a superfamily of at least 11 isozymes catalyzing the hydrolysis of cAMP and/or cGMP. PDE4 is a major cAMP-metabolizing enzyme in immune and inflammatory cells, airway smooth muscle, and pulmonary nerves. Based on its cellular and tissue distribution, selective inhibitors of this enzyme suppress mediator release from inflammatory cells (Hatzelmann and Schudt, . J Pharmacol Exp Ther 2001; 297:267-79, Marx et al., Pulm Pharmacol Ther 2002; 15:7-15, Kuss et al., J Pharmacol Exp Ther 2003; 307:373-85). They show a broad spectrum of activity in animal models of COPD (Billah et al., J Pharmacol Exp Ther 2002; 302:127-37, Kuss et al., J Pharmacol Exp Ther 2003; 307:373-85). The class-associated side effects, mainly nausea and emesis, appear to have been at least partially overcome by the so-called "second-generation" PDE4 inhibitors. Current clinical studies convincingly indicate the therapeutic usefulness of PDE4 inhibitors both in asthma and in COPD (Dyke and Montana, Expert Opin Investig Drugs 2002; 11:1-13, Grootendorst et al., Pulm Pharmacol Ther 2003; 16:341-7, Spina, Drugs 2003; 63:2575-94). Efforts to minimize or eliminate the above-mentioned adverse events sometimes associated with PDE4 inhibitors have included creating inhibitors which do not penetrate the central nervous system, and administering PDE4 inhibitors by inhalation rather than orally. Inhibitors of the isoenzyme PDE4 reduce the inflammatory processes both in asthma and COPD. Thus, these effects of PDE4 inhibitors result in an improved bronchial function in patients suffering from bronchial asthma or COPD.

Anticholinergic medications have been accepted as an important treatment modality in COPD and chronic asthma. The anticholinergic bronchodilator, the muscarinic receptor antagonist, used in this invention will be a long-acting compound. Any compound of this type can be used in this combination therapy approach. By long-lasting it is meant that the drug will have an effect on the bronchi that lasts around 12 hours or more, up to 24 hours. The recently approved long acting inhaled anticholinergic drug, tiotropium, produces sustained bronchodilation throughout the 24 hour day (Calverley et al., Thorax 2003; 58:855-60).

Glycopyrrolate belongs to the so-called anticholinergic drugs and antagonizes the neurotransmitter acetylcholine at its receptor site. This effect leads to a considerable bronchodilatation and a reduced mucus secretion. Glycopyrrolate, a quaternary ammonium compound, consists of four stereoisomers. It is poorly absorbed from mucus membranes, thus reducing anticholinergic side effects (Ali-Melkkila et al., Acta Anaesthesiol Scand 1993; 37:633-42). Glycopyrrolate possesses no selectivity in its binding to the $M_1$-$M_3$ receptors. Kinetics studies, however, showed that glycopyrrolate dissociates slowly from $M_3$ muscarinic receptors (Haddad et al., Br J Pharmacol 1999; 127:413-20). Similarly to tiotropium, this behavior explains glycopyrrolate's relative receptor selectivity and its long duration of action. Indeed, there is evidence that racemic glycopyrrolate produces considerable and long-lasting bronchodilatory effects both in asthmatic and in COPD patients (Walker et al., Chest 1987; 91:49-51, Schroeckenstein et al., J Allergy Clin Immunol 1988l; 82:115-9, Gilman et al., Chest 1990; 98:1095-8, Cydulka and Emerman, Ann Emerg Med 1995; 25:470-3). As asthma and COPD are characterized by increased mucus secretions, the antisecretory effect of anticholinergics such glycopyrrolate is an additional advantage for their use in the therapy of these diseases.

Current treatments for asthma and COPD are not satisfactory. Given the high prevalence of these diseases, improved, more effective and more convenient therapeutic interventions are highly desirable. The problem underlying the present invention was to provide such improved therapeutic alternatives with higher efficiency and reduced side effects.

The problem is solved by a new combination drug comprising a PDE4 inhibitor and an anticholinergic, which is superior to monocompounds with respect to therapeutic efficacy, onset and duration of action, or side-effects.

Surprisingly it has been revealed that the use of a combination comprising topical (inhaled) anticholinergics such as racemic glycopyrrolate, or its enantiomers, especially R,R-glycopyrrolate, or its diastereoisomers or their physiologically acceptable salts and inhaled/oral phosphodiesterase (PDE) 4 inhibitors such as AWD12-281 or Roflumilast or their physiologically acceptable salts results in a more effective and safer treatment of bronchial asthma and chronic obstructive pulmonary diseases (COPD) which allows for lower doses or which decreases side-effects.

The pharmacodynamic properties of both drug classes, anticholinergics (especially R,R-glycopyrrolate) and PDE4 inhibitors complement one another and result in more efficacious treatment of the mentioned diseases. Additionally, the patients' compliance is also increased. The PDE4 inhibitor useful in this invention may be any compound that is known to inhibit the PDE4 enzyme and which is discovered to act as highly specific PDE4 inhibitors and which is preferably used for inhalation. For example, preclinical and clinical studies with the highly potent and selective PDE4 inhibitor AWD 12-281 showed that this compound has a good preclinical and clinical efficacy. In Brown Norway rats, AWD 12-281 suppressed allergen-induced airway eosinophilia with an ID50 of 7 μg/kg when administered intrapulmonary. The ID50 value of the known corticosteroid beclomethasone was comparable (0.1 μg/kg). Due to its unique metabolic profile, the compound has a suitable safety profile after topical (nasal or inhaled) administration. When AWD 12-281 is given to dogs by inhalation, no emesis was induced up to the highest feasible dose (15 mg/kg) indicating that AWD 12-281 is useful for inhaled treatment of asthma and COPD (Kuss et al., J Pharmacol Exp Ther 2003; 307:373-85).

EXPERIMENTAL PART

The influence of R,R-glycopyrrolate in combination with PDE4 inhibitors on TNF secretion was investigated by using human peripheral blood mononuclear cells (PBMCs). The study was approved by our institutional Ethics Committee according to the International Declarations of Helsinki and Tokyo.

PBMCs were isolated from heparinized blood samples of healthy donors by density gradient centrifugation. An equal volume of Hanks buffer (Life Technologies, Heidelberg, Germany) is added to heparinized whole blood samples. 15 ml Histopaque-1077 (Sigma, Deisenhofen, Germany) are overlayed with a maximum of 40 ml of blood/Hanks mixture were centrifuged for 30 min at room temperature (2000 rpm). A visible band containing PBMCs is transferred to a fresh tube and washed twice with Hanks-buffer. Finally cells are seeded in RPMI 1640 Medium (Life Technologies, Heidelberg, Germany) with Glutamax I (Gibco BRL, Eggenstein) and 10% fetal calf serum (Boehringer Mannheim, Penzberg, Germany). After isolated, PBMCs were cultured in RPMI 1640 medium supplemented with 10% fetal calf serum (FCS) at 37° C. 5% $CO_2$ overnight. PBMCs were isolated from other cells by adherence method, non-adherent cells were removed by changing the medium.

Cells are re-suspended at 106 cells/ml and incubated in 500 µl volumes in 24-well tissue culture plates (Falcon Becton Dickinson Labware) at 37° C., 5% $CO_2$. After pre-incubation with test substances (0.5 µl/500 µl medium) for 30 min, cells were stimulated with lipopolysaccharide (LPS) (1 µg/ml). At indicated times cells were sedimented by centrifugation, the supernatants were harvested and kept frozen at −80° C. until protein determination; the cells were lysed by RLT lysis Buffer (Qiagen, Hilden, Germany) and frozen at −80° C. until analysis.

Cytokine measurements in culture supernatants are done by sandwich ELISA using matched antibody pairs (Pharmingen, Heidelberg, Germany). ELISA plates (Maxisorb, Nunc) are coated overnight with anti-cytokine monoclonal antibody (mAb) in 0.1 M carbonate buffer, pH 9.5. After being washed, plates are blocked with Assay Diluent (Pharmingen, Heidelberg, Germany) for 1 h and washed again. Appropriately diluted supernatant samples and standards are distributed in duplicates and the plates are incubated for 2 h at room temperature. Plates are washed, incubated for 1 h with working detector (biotinylated anti-cytokine antibody and Avidin-horseradish peroxidase conjugate). After washing, substrate (TMB and hydrogen peroxide) is added. The reaction is stopped by adding of 1M $H_3PO_4$. Plates are read at 450 nm (reference 570 nm) in a microplate reader (Dynatech). The results are expressed as a percentage of the control level of cytokines production by cells stimulated in the absence of the compound.

Upon LPS-stimulation, basal TNFα release from monocytes increased from 328 pg/ml up to 7,258 pg/ml. R,R-glycopyrrolate alone did not influence the LPS-induced TNFα release up to 10 µmol/l. The PDE4 inhibitor rolipram inhibited the TNFα release in a concentration-dependent manner. The $IC_{35}$ value of rolipram amounted to 68.9±15.2 nmol/l. The simultaneous addition of 10 µmol/l of R,R-glycopyrrolate surprisingly and highly significantly reduced the $IC_{35}$ to 1.70±1.18 nM (p=0.0151).

These results show that R,R-glycopyrrolate enhances the anti-inflammatory activity of PDE4 inhibitors significantly and surprisingly in an overadditive manner.

Both the anticholinergic and inhaled/oral PDE4 inhibitors can effectively be used in the treatment of various equine airway diseases. Activated neutrophils are recruited to the lungs of horses with COPD that may contribute to inflammation and lung damage. It has been demonstrated that PDE4 inhibitors may reduce neutrophil activation in vivo in horses with COPD (Rickards et al., J Vet Pharmacol Ther 2001; 24:275-81).

The combination therapy contemplated by this invention comprises administering a PDE4 inhibitor with a long-acting anticholinergic bronchodilator to prevent onset of a pulmonary disease event or to treat an existing condition and to reduce airway inflammation. The compounds may be administered together in a single dosage form. Or they may be administered in different dosage forms. They may be administered at the same time. Or they may be administered either close in time or remotely, such as where one drug is administered in the morning and the second drug is administered in the evening. The combination may be used prophylactically or after the onset of symptoms has occurred. In some instances the combination(s) may be used to prevent the progression of a pulmonary disease or to arrest the decline of a function such as lung function.

These drugs, the anticholinergics and the PDE4 inhibitors, are usually administered as an aerosol with or without propellant, or as an inhaled powder, for instance with the Novolizer®. This invention contemplates either co-administering both drugs in one delivery form such as an inhaler, which is putting both drugs in the same inhaler. Formulations are within the skill of the art (for instance contain excipients like lactose monohydrate).

The active ingredients may be given from 1 to 8 times a day, sufficient to exhibit the desired activity. Preferably, the active components are given about once or four times a day, more preferably once or twice a day.

The PDE4 inhibitor can be administered in an amount of between 200 and 5.000 µg/day adult human with the preference of 500 to 2.000 µg/day in dependence of the intensity of the airway inflammation. The PDE4 inhibitor, for example roflumilast can be administered inhaled or orally. The inhaled anticholinergic drug, racemic glycopyrrolate, one of its enantiomers, especially R,R-glycopyrrolate or one of its diastereoisomers or a mixture thereof and its salts, solvates and hydrates can be administered in an amount of between 5 and 500 µg/day adult human with the preference of 15 to 300 µg/day. A dosage range between 5 and 100 µg/day is especially preferred.

It is contemplated that both active agents would be administered at the same time, or very close in time. Alternatively, one drug could be taken in the morning and one later in the day. Or in another scenario, one drug could be taken twice daily and the other once daily, either at the same time as one of the twice-a-day dosing occurred, or separately. Preferably both drugs would be taken together at the same time.

For the veterinary use, the anticholinergic, especially R,R-glycopyrrolate can be given to horses in an amount of 1-32 µg/kg/day with the preference between 4 and 16 µg/kg/day alone or in combination with an inhaled PDE4 inhibitor administered in an amount of between 4 and 100 µg/day adult human with the preference of 10 to 40 µg/day in dependence of the intensity of the airway inflammation.

The invention is illustrated by but not restricted to the following example.

Powder inhalation with 50 µg R,R-glycopyrrolate and 500 µg AWD 12-281 per single dose A quantity of 50 g micronized R,R-glycopyrrolate is mixed with 100 g alpha lactose monohydrate, the mixture is given on a sieve of 0.5 mm mesh size and finally mixed again. 500 g micronized AWD 12-281 is mixed with 1000 g alpha lactose monohydrate, the mixture is given on a sieve of 0.8 mm mesh size and finally mixed again. The two mixtures received are blended and filled up with alpha lactose monohydrate to 12000 g. Subsequently, it is mixed again and the powder mixture received is filled in powder inhalers releasing 12 mg of powder per single dose. Per single dose, 50 µg R,R-glycopyrrolate and 500 µg AWD 12-281 are released from a powder inhaler and supplied to the patient's airways.

The invention claimed is:

1. A combination of topical R,R-glycopyrrolate or a physiologically acceptable salt thereof with rolipram or a physiologically acceptable salt thereof for the treatment of bronchial asthma or chronic obstructive pulmonary disease (COPD).

2. The combination according to claim 1 wherein the daily dose of R,R-glycopyrrolate is from 5 to 500 µg and the amount of rolipram is between 200 and 5,000 µg.

3. The combination according to claim 1 wherein the daily dose of R,R-glycopyrrolate is from 5 to 100 µg and the amount of rolipram is between 200 and 5,000 µg.

4. A pharmaceutical for the treatment of asthma or COPD containing topical R,R-glycopyrrolate or a physiologically acceptable salt thereof and at least rolipram or a physiologically acceptable salt thereof.

5. The pharmaceutical according to claim 4, wherein the R,R-glycopyrrolate, rolipram and/or physiologically acceptable salts thereof are available in an appropriate particle size dispersion when inhaled.

6. The pharmaceutical according to claim 4, that is an inhalable aerosol with or without propellant.

7. The pharmaceutical according to claim 4 that is an inhalable dry powder.

8. The pharmaceutical according to claim 4 that is an inhalable suspension or solution.

9. The pharmaceutical according to claim 4, presented in an inhaler.

10. The pharmaceutical according to claim 4, wherein the R,R glycopyrrolate, rolipram and/or physiologically acceptable salts thereof are presented in fixed or free combination for simultaneous, sequential or separate administration together with the usual excipients, adjuncts, and additives in a pharmaceutical form suitable for inhalative application.

11. The combination according to claim 2, wherein the daily dose of R,R glycopyrrolate is from 15 to 300 µg.

12. The combination according to claim 2, wherein the daily dose of the rolipram is from 500 to 2,000 µg.

13. A method of treating asthma or COPD in a mammal comprising administering an effective amount of a combination of topical R,R-glycopyrrolate or a physiologically acceptable salt thereof and rolipram or a physiologically acceptable salt thereof to said mammal.

14. The method according to claim 13 wherein the mammal is a human or a horse.

15. The method according to claim 13 wherein the daily dose of R,R-glycopyrrolate is between 5 and 500 µg and the daily dose of rolipram is between 200 and 5,000 µg.

16. The method according to claim 13 wherein the daily dose of R,R-glycopyrrolate is between 5 and 100 µg and the daily dose of rolipram is between 200 and 5,000 µg.

* * * * *